United States Patent
Clement et al.

(10) Patent No.: US 6,398,801 B1
(45) Date of Patent: Jun. 4, 2002

(54) TREATMENT OF VASCULAR LESIONS

(75) Inventors: Robert Marc Clement; Michael Noel Kiernan; Kelvin Donne, all of Swansea (GB)

(73) Assignee: ICN Photonics Limited, Wales (GB)

( * ) Notice: Subject to any disclaimer, the term of this patent is extended or adjusted under 35 U.S.C. 154(b) by 0 days.

(21) Appl. No.: 09/194,529

(22) PCT Filed: May 29, 1997

(86) PCT No.: PCT/GB97/01458

§ 371 (c)(1),
(2), (4) Date: Feb. 14, 2001

(87) PCT Pub. No.: WO97/45165

PCT Pub. Date: Dec. 4, 1997

(30) Foreign Application Priority Data

May 29, 1996 (GB) .............................................. 9611180

(51) Int. Cl.[7] ........................ A61N 65/067; A61B 18/18
(52) U.S. Cl. ................. 607/89; 606/9; 606/11
(58) Field of Search ...................... 606/2, 9, 11, 13–18; 372/53, 54; 607/89, 91

(56) References Cited

U.S. PATENT DOCUMENTS

| | | | | |
|---|---|---|---|---|
| 3,725,733 | A | * 4/1973 | Mack et al. | 315/228 |
| 4,733,660 | A | 3/1988 | Itzkan | |
| 4,973,848 | A | 11/1990 | Kolobanov et al. | |
| 4,977,571 | A | * 12/1990 | Furumoto et al. | 372/54 |
| 5,066,293 | A | * 11/1991 | Furumoto et al. | 606/9 |
| 5,109,387 | A | * 4/1992 | Garden et al. | 372/53 |
| 5,287,380 | A | 2/1994 | Hsia | |
| 5,586,981 | A | * 12/1996 | Hu | 606/9 |
| 5,599,342 | A | * 2/1997 | Hsia et al. | 606/9 |

FOREIGN PATENT DOCUMENTS

| | | |
|---|---|---|
| DE | 02B27/00 | 9/1991 |
| EP | 0165060 B1 | 6/1985 |
| EP | 0284330 A1 | 3/1988 |
| EP | 0320080 A1 | 5/1988 |
| EP | 0443033 A1 | 9/1990 |
| EP | 0429297 A2 | 11/1990 |
| NL | 9300064 | 1/1993 |
| WO | WO87/04632 | 8/1987 |
| WO | WO88/00072 | 1/1988 |
| WO | WO91/12050 | 8/1991 |
| WO | WO91/13652 | 9/1991 |
| WO | WO95/19808 | 7/1995 |
| WO | WO96/22813 | 8/1996 |
| WO | WO96/25979 | 8/1996 |

OTHER PUBLICATIONS

"Luminescent Characteristics of Flashlamps for Dye Lasers", by Maeda, Okada, Fujiwara, Uchino, and Miyazoe, Jan. 7, 1975, Kyushu Univ., Fukuoka,.

NBS Technical Note 603, "Construction of a Flashlamp–pumped Dye Laser and an Acousto–optic modulator for mode–locking", Jul. 1971, by Jennings and Baldwin.

"Tunable Dye Lasers" by D.J. Bradley, Queen's University, Belfast.

* cited by examiner

*Primary Examiner*—Roy Gibson
(74) *Attorney, Agent, or Firm*—Robert D. Fish; Sandra P. Thompson

(57) ABSTRACT

Vascular lesions are treated by using an apparatus which comprises a dye laser, one or more flashlamps, and at least one pulse generating circuit for driving the flashlamps, the pulse generating circuit arranged to produce driving current pulses having a risetime of less than 100 microseconds resulting in corresponding laser output pulses, having a risetime of less than 100 microseconds.

9 Claims, 2 Drawing Sheets

TREATMENT OF VASCULAR LESIONS

BACKGROUND OF THE INVENTION

1. Field of the Invention

The present invention relates to the treatment of vascular lesions using laser radiation.

2. State of the Art

The use of flashlamp pumped dye lasers has become the preferred form of treatment for a range of vascular lesions of the human body. In this treatment, a flashlamp is driven by a short pulse to excite or pump a laser light cell containing an appropriate dye solution, in order to emit a corresponding pulse of laser light at a predetermined wavelength, which is directed at the lesion to be treated; a preferred wavelength is 585 nm. Hitherto, it has been the accepted approach to maximise the temporal pulse length of the laser output pulse, with the aim of extending the period for which the target blood vessels are at elevated temperature and therefore increasing the probability that necrosis of the blood vessel (and hence permanent removal of the lesion) will occur. Accordingly, previous approaches have involved the use of laser output pulses of some 450 to 500 microseconds duration.

We have now devised an alternative approach, in the use of flashlamp pumped dye lasers, which results in more effective treatment of vascular lesions.

SUMMARY OF THE INVENTION

In accordance with this invention as seen from one aspect, there is provided a flashlamp pumped dye laser system which comprises:

(a) a dye laser;

(b) one or more flashlamps for exciting the dye laser; and (c) at least one pulse generating circuit for driving the or each said flashlamp, the pulse generating circuit being configured so as to provide a driving current having a risetime of less than 100 microseconds arranged to produce corresponding laser output pulses from the dye laser having a risetime of less than 100 microseconds.

Thus, we have discovered that a more effective treatment of vascular lesions can be achieved by significantly reducing the risetime of the laser output pulse which is most conveniently achieved using a driving circuit in which the current rises to a maximum rapidly, whereby the laser output follows closely the risetime of the driving current pulse. Hitherto, the laser output pulse has exhibited a risetime generally of 200 to 250 microseconds, the overall pulse duration being of the order of 450 to 500 microseconds. In systems which allegedly produce a rapid laser pulse risetime, specially configured laser arrangement and driving circuitry have been proposed (such as for example the arrangement disclosed in U.S. Pat. No. 5,287,380 which proposes a ramp pulse rising continuously throughout the laser pulse). The present invention provides the required performance in a simple and elegant manner.

Preferably, in the system in accordance with the present invention, the laser output pulse (and also preferably the drive current pulse) has risetime of less than 80 microseconds. We believe that there is an optimum risetime within the range of 30 to 80 microseconds and most preferably at substantially 50 microseconds. Preferably the laser output pulse maintains its maximum output level for 120 to 1000 microseconds, preferably 120 to 200 microseconds, and most preferably 150 microseconds.

Use of the system of the present invention extends the period for which the target blood vessel will be above a threshold temperature, so that necrosis can occur. Also, the significantly faster rise in temperature of the target blood vessel produces a faster increase of pressure due to local blood vaporisation, thus increasing the probability of vessel rupture and hence necrosis.

Also, in accordance with the present invention, as seen from a second aspect, there is provided a method of cosmetic treatment of vascular lesions, comprising directing pulses of radiation from a flashlamp pumped dye laser toward the lesions, the laser output pulses having a risetime of less than 100 microseconds. Preferably, the laser output pulse has a risetime of less than 80 microseconds. There is an optimum risetime within the range of 30 to 80 microseconds and most preferably at substantially 50 microseconds.

It is preferred that the laser output pulse maintains its maximum output level at a pulse duration in the range 120 to 1000 microseconds, preferably 120 to 200 microseconds, and most preferably 150 microseconds.

In systems which have been used hitherto, it has been known to use a drive circuit in which one side of the flashlamp is connected through a transformer secondary winding and a resistor to a high voltage supply, a capacitor is connected from the resistor to the ground side of the circuit, and the other side of the flashlamp is connected through an inductor to the ground side. A short trigger pulse is applied to the transformer primary winding, so that a pulse of radiation is emitted from the flashlamp. The inductor in the ground side circuit of the flashlamp has the effect of extending the pulse duration.

In accordance with the present invention as seen from a third aspect, there is provided a flashlamp drive circuit, comprising at least one flashlamp having one side connected through a transformer secondary winding, and a resistor to a high voltage supply, a capacitor connected from the resistor to the ground side and the flashlamp having its other side connected directly to the ground side circuit. It is preferred that two such circuits are provided, connected to each other.

In this circuit, because of the substantial absence of any inductance in the ground side circuit of the flashlamp, the pulse which drives the flashlamp exhibits a substantially reduced risetime. The circuit is configured in such a way that the rising portion of the current pulse is substantially unrestricted leading to a relatively rapid risetime to a peak value before subsequently tailing off. The rise time of the driving current pulse in U.S. Pat. No. 5,287,380 is controlled so as to be increasing throughout the duration of the laser output pulse.

Embodiments of the present invention will now be described by way of example only and with reference to the accompanying drawings.

DETAILED DESCRIPTION OF THE PREFERRED EMBODIMENTS

Figure 1:
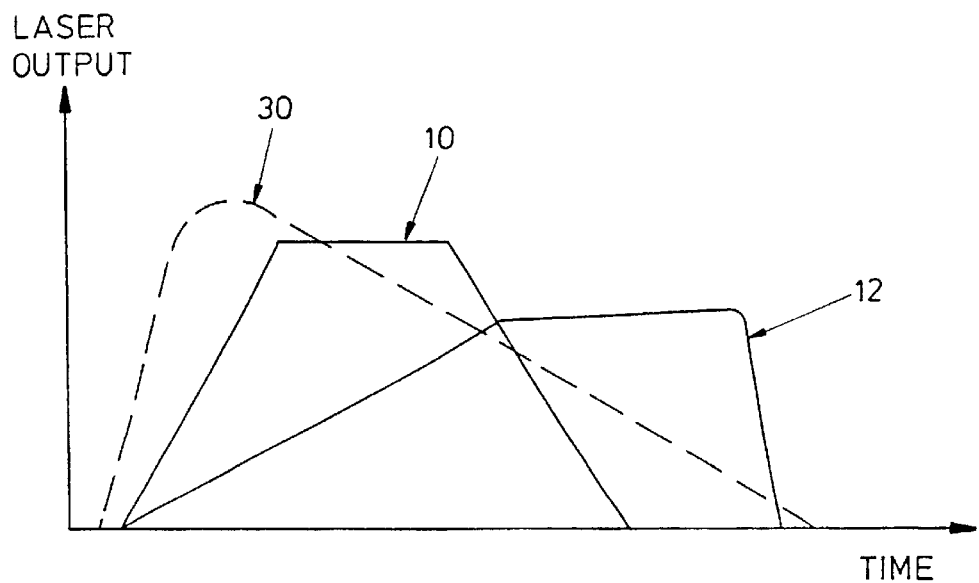
FIG. 1 is a waveform diagram comparing the laser output pulses produced, respectively, in hitherto-known systems and in the method and apparatus according to the present invention.

Referring to FIG. 1, a flashlamp pumped dye laser system in accordance with the present invention generates a laser output pulse of the waveform shown generally at 10, in contrast with the previously-used pulse shown at 12. Thus, the previously-used pulse 12 typically has a resistor of 200 to 250 microseconds and an overall duration of 450 to 500 microseconds. The pulse 10 in accordance with this invention has a substantially shorter risetime of less than 100 microseconds and preferably 50 to 80 microseconds, followed by a plateau of 120 to 200 microseconds, and preferably 150 microseconds. (The plateau can however be maintained for a longer duration, such as for example up to 1000 microseconds). The driving circuit (shown in FIG. 4 and discussed in detail below) is configured such that the risetime of the driving current pulse 30 is correspondingly brief and typically fractionally leads the rise of the laser pulse.

Figure 2:
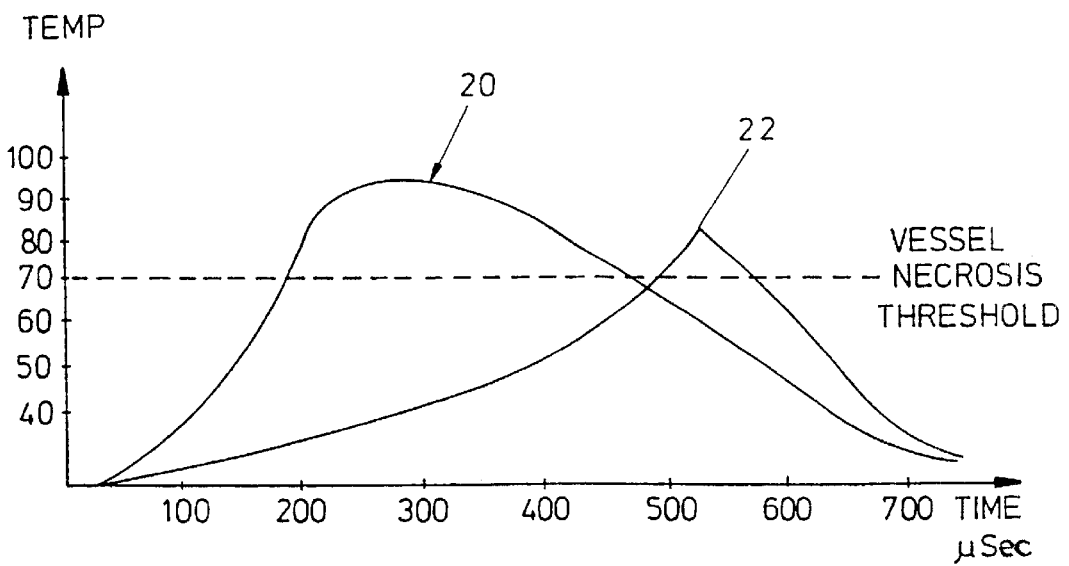
FIG. 2 is a waveform diagram comparing the variations of blood vessel temperature which occur when using, respectively, known systems and method and apparatus according to the present invention.

As shown in FIG. 2, the previously-known laser output pulse 12 of FIG. 1 produces a gradual rise in target vessel temperature, as shown by the curve 22, followed by a relatively rapid drop in temperature. The temperature exceeds the necrosis threshold for a relatively short time. By contrast, the laser output pulse 10 of the present invention (as driven by the drive current as specified) produces a relatively rapid rise in the target vessel temperature, and this temperature remains above the necrosis threshold for much longer, as shown by the curve 20.

Figure 3:
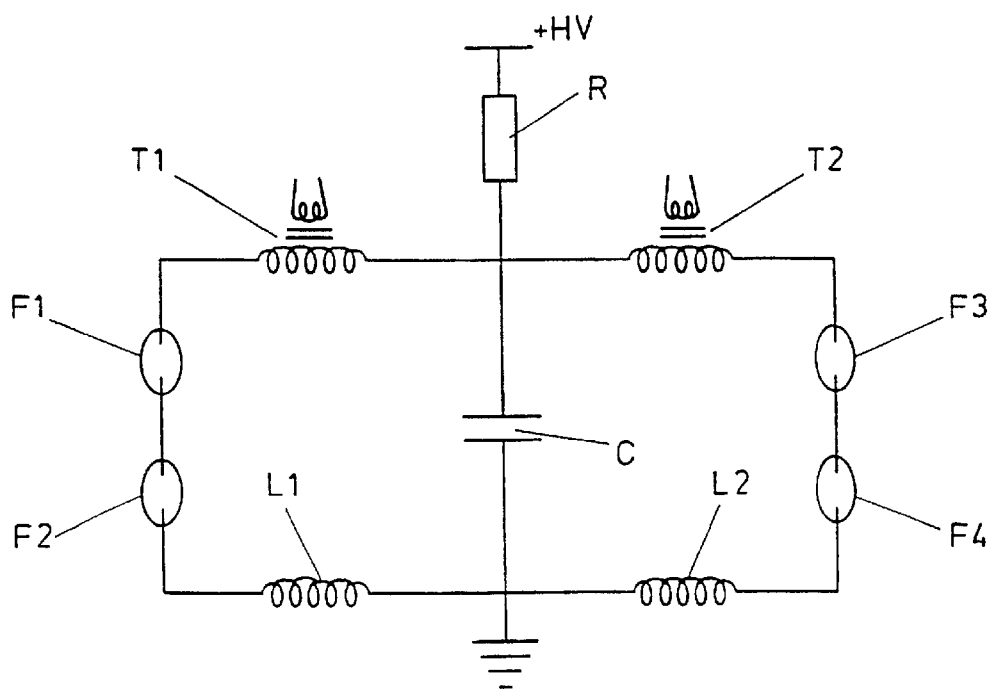
FIG. 3 is a diagram of a typical flashlamp drive circuit used in known systems.

As shown in FIG. 3, previously a drive circuit has been used which comprises a resistor R and a capacitor C connected between a high voltage supply and ground. A first pair of flashlamps F1, F2 are connected in series with each other and are further connected on the one hand through the secondary winding of a transformer T1 to the resistor R, and on the other hand through an inductor L1 to the ground. A second pair of flashlamps F3, F4 are included in a similar circuit with a transformer T2 and inductor L2. The flashlamps are all positioned to pump the dye laser cell, and are triggered by the application of a short pulse to the primary windings of both transformers T1, T2.

Figure 4:
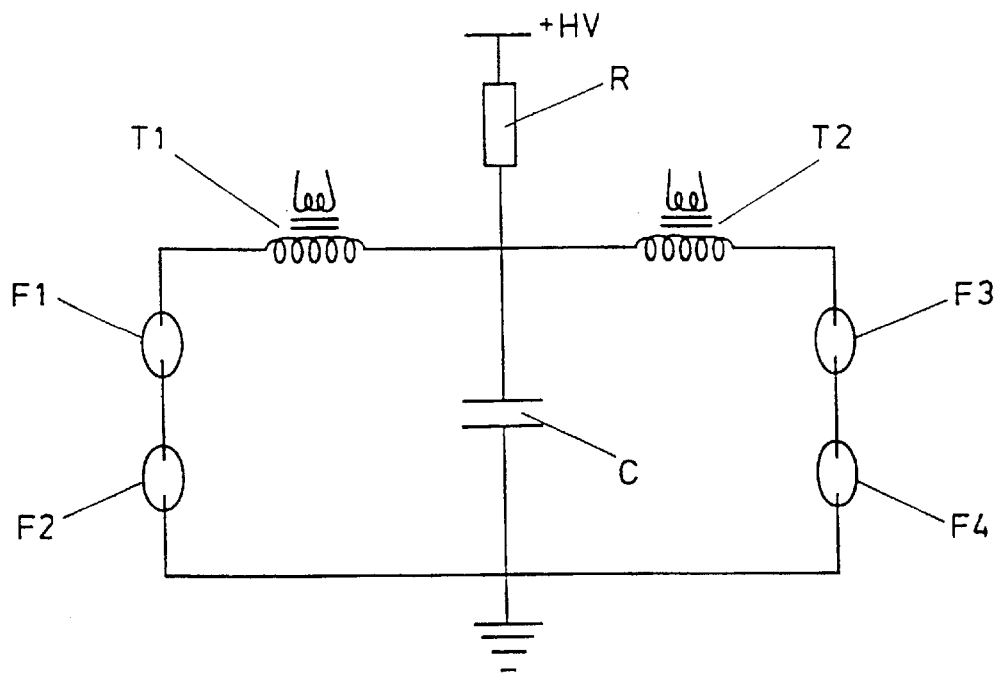
FIG. 4 is a diagram of the flashlamp drive circuit used in method and apparatus in accordance with the present invention.

As shown in FIG. 4, and in order to shorten the risetime of the current pulse which drives the flashlamps, the ground sides of flashlamps F2, F4 are connected directly to ground i.e. the ground side inductors L1, L2 are omitted. Also the inductances of the secondary windings of the transformers T1, T2 in FIG. 4 are substantially less than those of FIG. 3.

What is claimed is:

1. Apparatus for treating vascular lesions, which apparatus comprises:
   (a) a dye laser;
   (b) at least one flashlamp for exciting said dye laser; and
   (c) at least one pulse generating circuit for driving the, or each, said flashlamp, the pulse generating circuit being configured so as to provide driving current pulses having a risetime of less than 100 microseconds arranged to produce corresponding laser output pulses from the dye laser having a risetime of less than 100 microseconds;
wherein said pulse generating circuit is configured such that there is a substantial absence of inductance in the ground side circuit of the, or each, said flashlamp.

2. Apparatus for treating vascular lesions, which apparatus comprises:
   (a) a dye laser;
   (b) at least one flashlamp for exciting said dye laser; and
   (c) at least one pulse generating circuit for driving the, or each, said flashlamp, the pulse generating circuit being configured so as to provide driving current pulses having a risetime of less than 100 microseconds arranged to produce corresponding laser output pulses from the dye laser having a risetime of less than 100 microseconds;
wherein said pulse generating circuit comprises a voltage supply connected to one side of at least one said flashlamp through a transformer, the, or each, said flashlamp having its other side connected to the ground side of the circuit.

3. Apparatus according to claim 2, wherein the flashlamp is connected to the secondary winding of the transformer, a trigger pulse applied to the transformer primary winding triggering the flashlamp to excite the dye laser.

4. Apparatus according to claim 2, wherein said flashlamp is connected through said transformer and a resistor to said voltage supply.

5. Apparatus according to claim 4, wherein a capacitor is connected from said resistor to the ground side of said circuit.

6. Apparatus according to claim 1, which includes two said circuits.

7. Apparatus for treating vascular lesions, which apparatus comprises:
   (a) a dye laser;
   (b) at least one flashlamp for exciting said dye laser; and
   (c) at least one pulse generating circuit for driving the, or each, said flashlamp, the pulse generating circuit being configured so as to provide driving current pulses having a risetime of less than 100 microseconds arranged to produce corresponding laser output pulses from the dye laser having a risetime of less than 100 microseconds;
wherein an arrangement comprising a plurality of flashlamps is provided connected in series with one another, each flashlamp arrangement being driven by a respective pulse generating circuit.

8. Apparatus for treating vascular lesions, which apparatus comprises:
   (a) a dye laser;
   (b) at least one flashlamp for exciting said dye laser; and
   (c) at least one pulse generating circuit for driving the, or each, said flashlamp, the pulse generating circuit being configured so as to provide driving current pulses having a risetime of less than 100 microseconds arranged to produce corresponding laser output pulses from the dye laser having a risetime of less than 100 microseconds;
wherein said at least one flashlamp has one side thereof connected through a transformer and a resistor to a voltage supply;
said circuit further including a capacitor connected from said resistor to the ground side of said pulse generating circuit; and
said flashlamp having its other side connected to said ground side.

9. Apparatus according to claim 8, which includes two said circuits.

* * * * *